(12) United States Patent
Kohno et al.

(10) Patent No.: US 6,960,692 B2
(45) Date of Patent: Nov. 1, 2005

(54) DIARYL SULFIDE DERIVATIVE, ADDITION SALT THEREOF, AND IMMUNOSUPPRESSANT

(75) Inventors: Yasushi Kohno, Tochigi (JP); Naoki Ando, Gunma (JP); Kazuhiko Kuriyama, Tochigi (JP); Satoru Iwanami, Ibaraki (JP); Shinji Kudou, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 31 days.

(21) Appl. No.: 10/489,820

(22) PCT Filed: Sep. 25, 2002

(86) PCT No.: PCT/JP02/09865

§ 371 (c)(1),
(2), (4) Date: Mar. 17, 2004

(87) PCT Pub. No.: WO03/029205

PCT Pub. Date: Apr. 10, 2003

(65) Prior Publication Data

US 2004/0254222 A1 Dec. 16, 2004

(30) Foreign Application Priority Data

Sep. 27, 2001 (JP) .................................. 2001-297411
Jul. 25, 2002 (JP) .................................. 2002-216192

(51) Int. Cl.$^7$ .................. C07C 317/32; C07C 323/32; A61K 31/145; A61P 11/06; A61P 17/00
(52) U.S. Cl. ........................................ 564/341; 514/653
(58) Field of Search .......................... 564/341; 514/653

(56) References Cited

U.S. PATENT DOCUMENTS 5,284,971 A * 2/1994 Walker et al. ............... 562/429
5,604,229 A 2/1997 Fujita et al.

FOREIGN PATENT DOCUMENTS

EP 1 002 792 5/2000

* cited by examiner

*Primary Examiner*—Brian Davis
(74) *Attorney, Agent, or Firm*—Wenderoth, Lind & Ponack, L.L.P.

(57) ABSTRACT

The present invention provides diaryl sulfide derivatives that exhibit significant immunosuppressive effects with less side effects.

The diaryl derivatives of the present invention are represented by the following general formula (1):

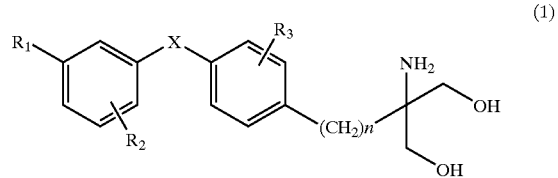

(1)

One example is 2-amino-2-[4-(3-benzyloxyphenylthio)-2-chlorophenyl]propyl-1,3-propanediol.

16 Claims, 2 Drawing Sheets

DIARYL SULFIDE DERIVATIVE, ADDITION SALT THEREOF, AND IMMUNOSUPPRESSANT

This is a 371 of PCT/JP02/09865, filed Sep. 25, 2002.

TECHNICAL FIELD

The present invention relates to diaryl sulfide derivatives, salts and hydrates thereof that are useful as an immunosuppressive agent.

TECHNICAL BACKGROUND

Immunosuppressive agents are widely used as a treatment for autoimmune diseases such as rheumatoid arthritis, nephritis, osteoarthritis and systemic lupus erythematosus, chronic inflammatory diseases such as inflammatory bowel disease, and allergic diseases such as asthma and dermatitis. Progress in medicine has led to an increase in the number of tissue and organ transplantations performed each year. In such a situation of modern medicine, having as much control as possible over the rejection following transplantation is a key to successful transplantation. Immunosuppressive agents also play a significant role to this end.

Among immunosuppressors commonly used in organ transplantation are antimetabolites, such as azathioprine and mycophenolate mofetil, calcineurin inhibitors, such as cyclosporin A and tacrolimus, and corticosteroid, such as prednisolone. Despite their popularity, some of these drugs are not effective enough while others require continuous monitoring of the blood drug level to avoid renal failure and other serious side effects. Thus, none of conventional immunosuppressive agents are satisfactory in view of efficacy and potential side effects.

Multiple drug combined-therapy, in which different immunosuppressive drugs with different mechanisms of action are used, is becoming increasingly common with the aims of alleviating the side effects of the drugs and achieving sufficient immunosuppressive effects. Also, development of new types of immunosuppressive agents that have completely different mechanisms of action is sought.

In an effort to respond to such demands, the present inventors conducted a search for new types of immunosuppressive agents with main emphasis on 2-amino-1,3-propanediol derivatives.

While the use of 2-amino-1,3-propanediol derivatives as immunosuppressive agents has been disclosed in PCT publication WO94/08943 (YOSHITOMI PHARMACEUTICAL INDUSTRIES, Ltd., TAITO Co., Ltd.) and in Japanese Patent Publication No. Hei 9-2579602 (YOSHITOMI PHARMACEUTICAL INDUSTRIES, Ltd., TAITO Co., Ltd.), it has not been previously known that 2-amino-1,3-propanediol derivatives having a diaryl sulfide group, which are subjects of the present invention, can serve as an effective immunosuppressor.

DISCLOSURE OF THE INVENTION

Accordingly, it is an objective of the present invention to provide a diaryl sulfide derivative that exhibits significant immunosuppressive effects with little side effects.

In the course of studies on immunosuppressive agents that have different mechanisms of action from antimetabolites and calcineurin inhibitors, the present inventors discovered that novel diaryl sulfide derivatives that have a different structure from conventional immunosuppressors exhibit strong immunosuppressive effects. Specifically, the compounds are such that one of the aryl groups includes, at its para-position, a carbon chain with an aminopropanediol group and the other aryl group includes a substituent at its meta-position. This discovery led the present inventors to devise the present invention.

The present invention thus is an immunosuppressive agent containing as an active ingredient at least one of a diaryl sulfide derivative, a pharmaceutically acceptable salt and hydrate thereof, the diaryl sulfide derivative represented by the following general formula (1):

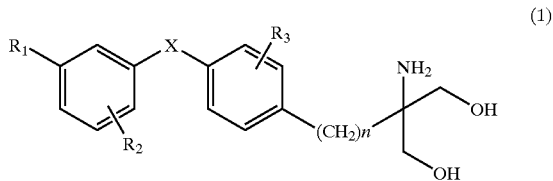

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxyl having 1 to 4 carbon atoms, hydroxy, benzyloxy, lower alkyl having 1 to 7 carbon atoms, phenyl, or lower alkoxymethyl having 1 to 4 carbon atoms; X is S, SO, or $SO_2$; and n is an integer from 1 to 4.

More specifically, the present invention is an immunosuppressive agent containing as an active ingredient at least one of a diaryl sulfide derivative, a pharmaceutically acceptable salt and hydrate thereof, the diaryl sulfide derivative represented by the following general formula (1a):

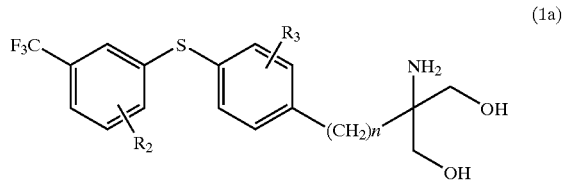

wherein $R_2$, $R_3$, and n are the same as defined above.

Furthermore, the present invention is an immunosuppressive agent containing as an active ingredient at least one of a diaryl sulfide derivative, a pharmaceutically acceptable salt and hydrate thereof, the diaryl sulfide derivative represented by the following general formula (1b):

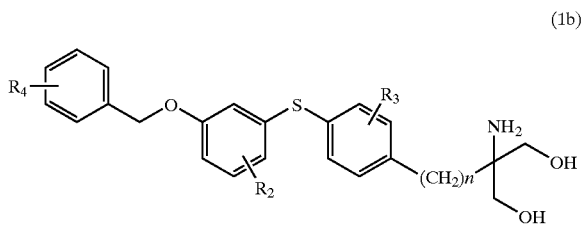

(1b)

wherein $R_2$, $R_3$, and n are the same as defined above; and $R_4$ is hydrogen, halogen, lower alkyl having 1 to 7 carbon atoms, lower alkoxy having 1 to 4 carbon atoms, or trifluoromethyl.

The compounds of the general formulae (1), (1a), and (1b) are each a novel compound.

Examples of the pharmaceutically acceptable salt of the compound of the general formula (1) include acid salts, such as hydrochloride, hydrobromide, acetate, trifluoroacetate, methanesulfonate, citrate, and tartrate.

BEST MODE FOR CARRYING OUT THE INVENTION

Figure 1:
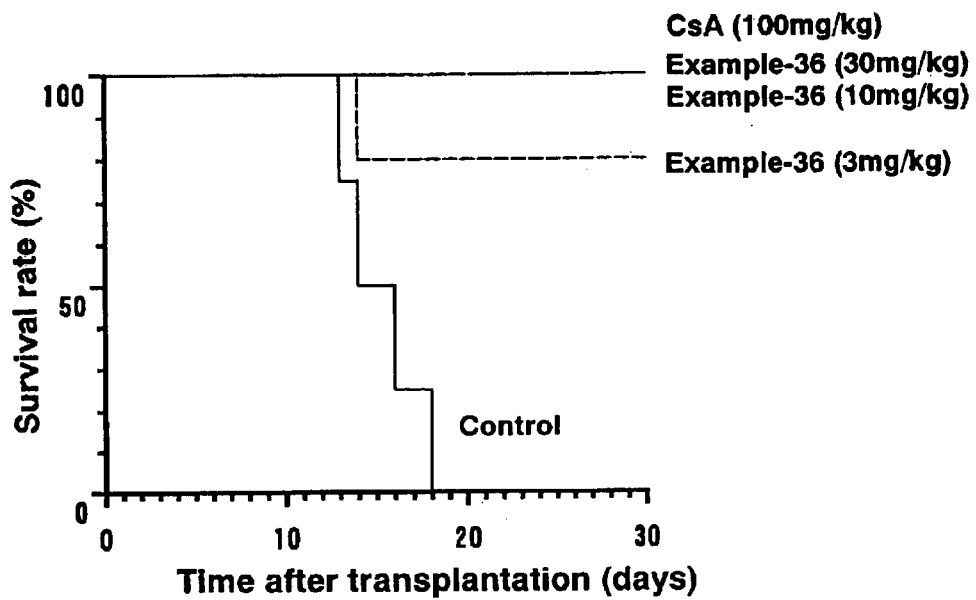
FIG. 1 is a graph showing activities of a test compound in a mouse skin graft model.

With regard to the general formula (1), the term 'halogen atom' encompasses fluorine, chlorine, bromine, and iodine atom. The term 'trihalomethyl group' encompasses trifluoromethyl and trichloromethyl. The phrase 'lower alkyl group having 1 to 7 carbon atoms' encompasses straight-chained or branched hydrocarbons having 1 to 7 carbon atoms, such as methyl, ethyl, propyl, isopropyl, butyl, t-butyl, pentyl, hexyl, and heptyl. The phrase 'substituted or unsubstituted phenoxy group' encompasses those that have, at any position of its benzene ring, a halogen atom, such as fluorine, chlorine, bromine and iodine, trifluoromethyl, lower alkyl having 1 to 4 carbon atoms, or lower alkoxy having 1 to 4 carbon atoms. The term 'aralkyl group' as in 'aralkyl group' or 'aralkyloxy group' encompasses benzyl, diphenylmethyl, phenethyl, and phenylpropyl. The term 'lower alkyl group' as used in 'lower alokoxy group having 1 to 4 carbon atoms,' 'lower alkylthio group having 1 to 4 carbon atoms,' 'lower alkylsulfinyl group having 1 to 4 carbon atoms,' or 'lower alkylsulfonyl group having 1 to 4 carbon atoms,' encompasses straight-chained or branched hydrocarbons having 1 to 4 carbon atoms, such as methyl, ethyl, propyl, isopropyl, and butyl. The phrase 'substituted or unsubstituted aralkyl group' encompasses those that have, at any position of its benzene ring, a halogen atom, such as fluorine, chlorine, bromine and iodine, trifluoromethyl, lower alkyl having 1 to 4 carbon atoms, or lower alkoxy having 1 to 4 carbon atoms.

According to the present invention, the compounds of the general formula (1) can be produced in the following pathways:

Synthetic Pathway 1

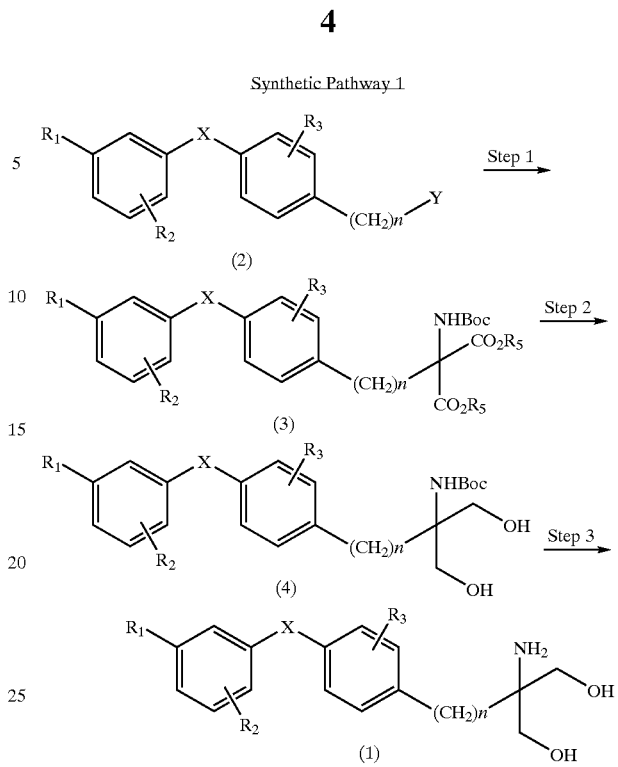

The compound involved in the synthetic pathway 1 that is represented by the following general formula (3):

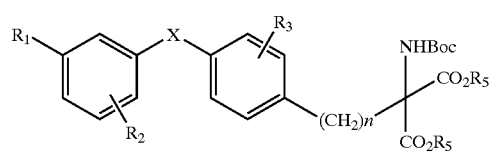

(wherein $R_5$ is lower alkyl having 1 to 4 carbon atoms; Boc is t-butoxycarbonyl; and $R_1$, $R_2$, $R_3$, X and n are the same as described above) can be prepared by reacting a compound of the following general formula (2):

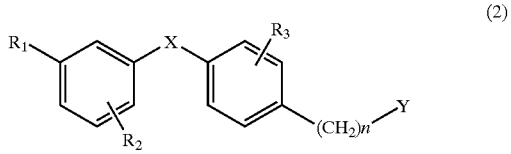

(wherein Y is chlorine, bromine, or iodine; and $R_1$, $R_2$, $R_3$, X and n are as described above) with a compound of the following general formula (5):

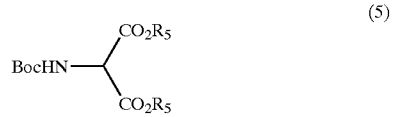

(wherein $R_5$ and Boc are as described above) in the presence of a base (Step 1).

This reaction can be carried out using a reaction solvent such as methanol, ethanol, 1,4-dioxane, dimethylsulfoxide (DMSO), N,N-dimethylformamide (DMF), or tetrahydrofuran (THF) at a reaction temperature of 0° C. to reflux temperature, preferably at a temperature of 80° C. to 100° C., in the presence of an inorganic base such as sodium hydride, potassium hydride, sodium alkoxide, and potassium alkoxide.

The compound involved in the synthetic pathway 1 that is represented by the following general formula (4):

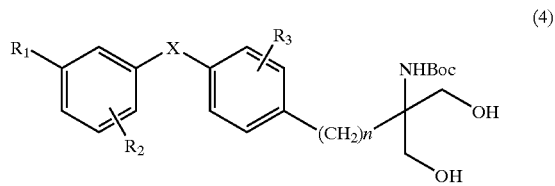

(4)

(wherein $R_1$, $R_2$, $R_3$, X, Boc, and n are as described above) can be prepared by the reduction of the compound of the general formula (3) (Step 2).

This reaction can be carried out at a reaction temperature of 0° C. to reflux temperature, preferably at room temperature, using an alkylborane derivative, such as borane ($BH_3$) and 9-borabicyclo[3.3.1]nonane (9-BBN), or a metal hydride complex, such as diisobutylaluminum hydride (($iBu$) $2AlH$), sodium borohydride ($NaBH_4$) and lithium aluminum hydride ($LiAlH_4$), preferably lithium borohydride ($LiBH_4$), and using a reaction solvent such as THF, ethanol and methanol.

The compound involved in the synthetic pathway 1 that is represented by the general formula (1):

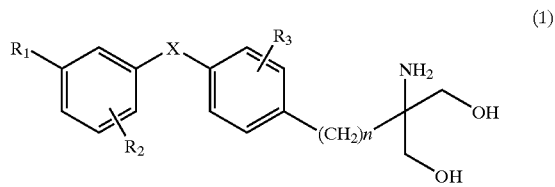

(1)

(wherein $R_1$, $R_2$, $R_3$, X and n are as described above) can be prepared by the acidolysis of the compound of the general formula (4) (Step 3).

This reaction can be carried out at a reaction temperature in the range of 0° C. to room temperature in an inorganic or organic acid, such as acetic acid, hydrochloric acid, hydrobromic acid, methanesulfonic acid and trifluoroacetic acid, or in a mixed solvent with an organic solvent such as methanol, ethanol, THF, 1,4-dioxane, and ethyl acetate.

Of the compounds of the general formula (3), those in which X is either SO or $SO_2$, namely, those represented by the following general formula (6):

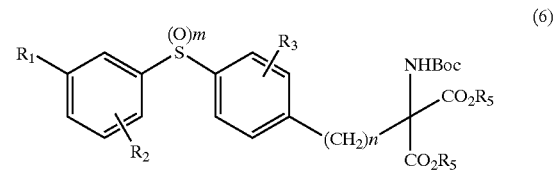

(6)

(wherein m is an integer of 1 or 2; and $R_1$, $R_2$, $R_3$, $R_5$, Boc, and n are as described above) may also be prepared by the oxidizing a compound represented by the following general formula (7):

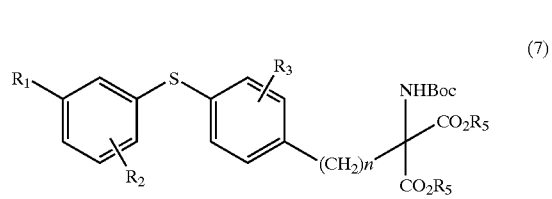

(7)

(wherein $R_1$, $R_2$, $R_3$, $R_5$, Boc, and n are as described above).

This reaction can be carried out using a reaction solvent, such as 1,4-dioxane, DMSO, DMF, THF, methylene chloride or chloroform, along with an oxidizing agent, such as potassium permanganate, m-chloroperbenzoic acid or aqueous hydrogen peroxide, at a reaction temperature of 0° C. to reflux temperature, preferably at room temperature.

Of the compounds of the general formula (1), those in which X is either SO or $SO_2$, namely, those represented by the following general formula (8)):

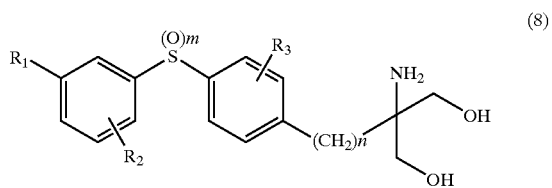

(8)

(wherein $R_1$, $R_2$, $R_3$, Boc, m, and n are as described above) may also be prepared by the following synthetic pathway:

Synthetic pathway 2

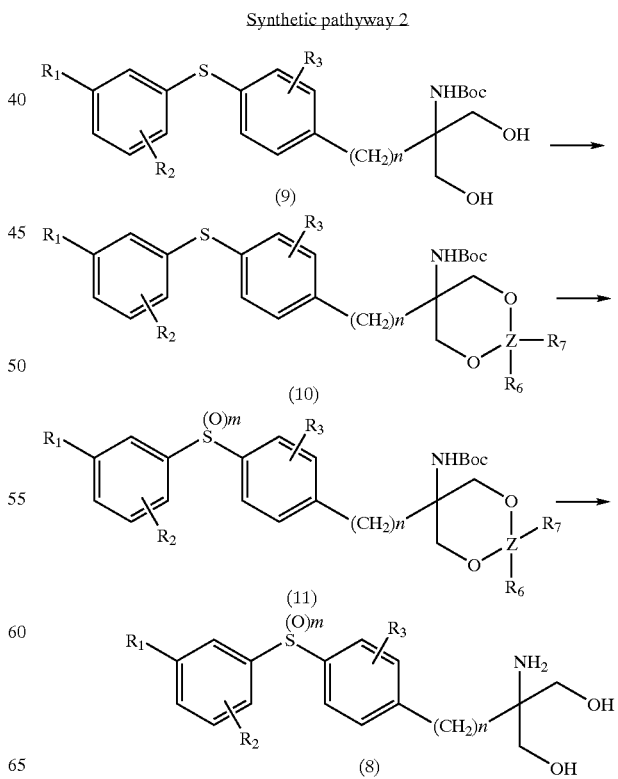

Specifically, a compound represented by the following general formula (9):

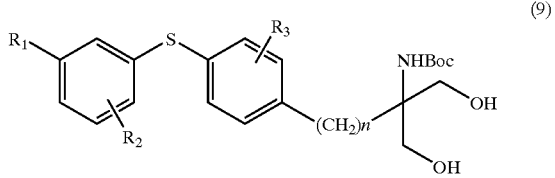
(9)

(wherein $R_1$, $R_2$, $R_3$, Boc, and n are as described above) can be reacted either with a compound represented by the following general formula (12):

(12)

(wherein $R_6$ and $R_7$ each independently represent hydrogen or lower alkyl having 1 to 4 carbon atoms), or with a compound represented by the following general formula (13):

(13)

(wherein $R_8$ is lower alkyl having 1 to 4 carbon atoms; and $R_6$ and $R_7$ are as described above), or with a compound represented by the following general formula (14):

(14)

(wherein $R_9$ is chlorine or trifluoromethanesulfonyloxy; and $R_6$ and $R_7$ are as described above) to produce a compound represented by the following general formula (10):

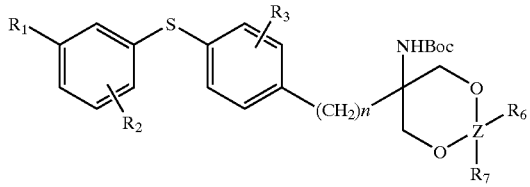
(10)

(whrein Z is carbon or silicon; and $R_1$, $R_2$, $R_3$, $R_6$, $R_7$, Boc, and n are as described above).

The reaction between the compound of the general formula (9) and the compound of the general formula (12) or the compound of the general formula (13) can be carried out at a reaction temperature in the range of room temperature to 100° C. either in the presence of a Lewis acid such as zinc chloride or in the presence of an acid catalyst such as camphorsulfonic acid, paratoluenesulfonic acid, and pyridinium paratoluenesulfonic acid, and may be carried out either in the absence of solvent or in the presence of a reaction solvent such as DMF, THF, and methylene chloride.

The reaction between the compound of the general formula (9) and the compound of the general formula (14) can be carried out at a reaction temperature of 0° C. to 100° C. in the presence of a base, such as triethylamine, pyridine, 2,6-lutidine, and imidazole, and can be carried out using a reaction solvent such as DMF, THF, methylene chloride, chloroform, and acetonitrile.

The compound involved in the synthetic pathway 2 that is represented by the following general formula (11):

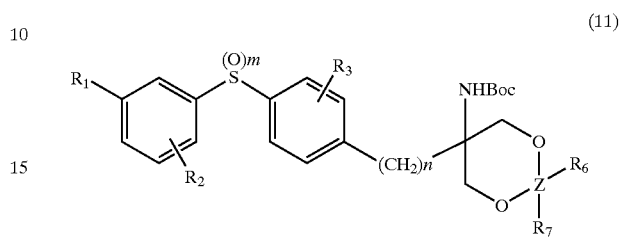
(11)

(wherein $R_1$, $R_2$, $R_3$, $R_6$, $R_7$, Z, Boc, m and n are as described above) can be prepared by the oxidizing the compound of the general formula (10).

This reaction can be carried out using a reaction solvent, such as 1,4-dioxane, DMSO, DMF, THF, methylene chloride or chloroform, along with an oxidizing agent, such as potassium permanganate, m-chloroperbenzoic acid or aqueous hydrogen peroxide, at a reaction temperature of 0° C. to reflux temperature, preferably at room temperature.

The compound of the general formula (8) involved in the synthetic pathway 2 can be prepared by the acidolysis, or desilylation followed by acidolysis, of the compound of the general formula (11).

This reaction can be carried out at a reaction temperature of 0° C. to room temperature in an inorganic or organic acid, such as acetic acid, hydrochloric acid, hydrobromic acid, methanesulfonic acid, trifluoroacetic acid, or in a mixed solution with an organic solvent, such as methanol, ethanol, THF, 1,4-dioxane, and ethyl acetate.

When Z in the general formula (11) is a silicon atom, the compound of the general formula (11) may also be synthesized by a reaction with potassium fluoride, cesium fluoride, or tetrabutylammonium fluoride, carried out at a temperature of 0° C. to room temperature in a solvent such as THF, DMF, 1,4-dioxane, followed by the above-described acidolysis.

EXAMPLES

The present invention will now be described with reference to examples, which are provided by way of example only and are not intended to limit the scope of the invention in any way.

Reference Example 1

2-chloro-4-[(3-trifluoromethyl)phenylthio]benzaldehyde

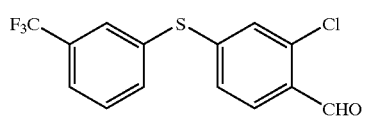

Potassium carbonate (2.76 g) was added to a solution of 2-chloro-4-fluorobenzaldehyde (1.15 g) and 3-(trifluoromethyl)thiophenol (1.33 g) in DMF (20 mL) and the mixture was stirred for 1 hour while heated to 120° C.

The reaction mixture was poured into water and was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=10:1). In this manner, the desired product (1.96 g) was obtained as a pale yellow oil.

Reference Examples 2 through 9

Using various thiophenols and aldehydes, the compounds shown in Table 1 below were each synthesized in the same manner as described above.

TABLE 1

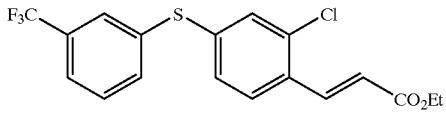

| Reference Example | R1 | R2 | R3 |
|---|---|---|---|
| 2 | CF$_3$ | H | H |
| 3 | CF$_3$ | H | CF$_3$ |
| 4 | CF$_3$ | CF$_3$ | H |
| 5 | CF$_3$ | CF$_3$ | Cl |
| 6 | MeO | H | H |
| 7 | MeO | H | Cl |
| 8 | MeO | H | CF$_3$ |
| 9 | Cl | Cl | H |

Reference Example 10

Ethyl 2'-chloro-4'-[(3-trifluoromethyl)phenylthio]cinnamate

Under argon, 60% sodium hydride (272 mg) was added to a solution of ethyl(diethylphosphono)acetate (1.35 mL) in THF (30 ml) at 0° C. and the mixture was stirred for 30 minutes. A solution of the compound of Reference Example 1 (1.96 g) in THF (15 mL) was then added dropwise. With the temperature maintained, the mixture was further stirred for 2 hours, followed by addition of water and then extraction with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=10:1). In this manner, the desired product (1.72 g) was obtained as a colorless oil.

Reference Examples 11 through 18

Using the compounds of Reference Examples 2 through 9, the compounds shown in Table 2 below were each synthesized in the same manner as described above.

TABLE 2

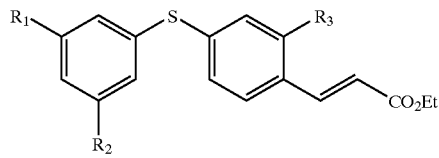

| Reference Example | R1 | R2 | R3 |
|---|---|---|---|
| 11 | CF$_3$ | H | H |
| 12 | CF$_3$ | H | CF$_3$ |
| 13 | CF$_3$ | CF$_3$ | H |
| 14 | CF$_3$ | CF$_3$ | Cl |
| 15 | MeO | H | H |
| 16 | MeO | H | Cl |
| 17 | MeO | H | CF$_3$ |
| 18 | Cl | Cl | H |

Reference Example 19

Ethyl 2'-chloro-4'-(3-trifluoromethylphenylthio)dihydrocinnamate

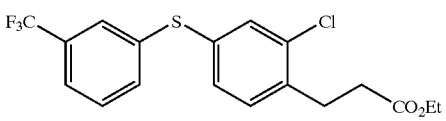

The compound of Reference Example 10 (1.72 g) was dissolved in ethanol (70 mL). Bismuth chloride (703 mg) was then added to the solution while the solution was stirred at 0° C. To the resulting mixture, sodium borohydride (673 mg) was added in small portions, and the mixture was stirred for 1 hour at the same temperature and subsequently for 3 hours at room temperature. Ice water was then added to the reaction mixture and the crystallized inorganic deposits were filtered out through celite. The filtrate was extracted with ethyl acetate. The organic phase was sequentially washed with water and a saturated aqueous solution of sodium chloride and was dried with anhydrous sodium sulfate. The solvent was removed by distillation under reduced pressure. In this manner, the desired product (1.50 g) was obtained as a colorless oil.

Reference Examples 20 through 25

Using the compounds of Reference Examples 11, 12, and 14 through 17, the compounds shown in Table 3 below were each synthesized in the same manner as described above.

TABLE 3

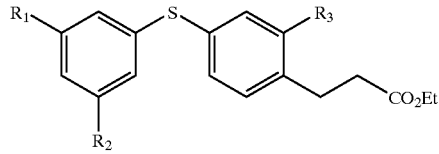

| Reference Example | R1 | R2 | R3 |
|---|---|---|---|
| 20 | CF$_3$ | H | H |
| 21 | CF$_3$ | H | CF$_3$ |
| 22 | CF$_3$ | CF$_3$ | Cl |
| 23 | MeO | H | H |

TABLE 3-continued

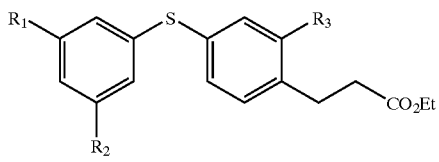

| Reference Example | R1 | R2 | R3 |
|---|---|---|---|
| 24 | MeO | H | Cl |
| 25 | MeO | H | CF$_3$ |

Reference Example 26

4'-(3-hydroxyphenylthio)dihydrocinnamic Acid

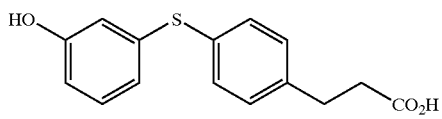

Under argon, a 1 mol/L solution of boron tribromide in methylene chloride (20 mL) was added to a solution of the compound of Reference Example 23 (3.20 g) in methylene chloride (50 mL), and the mixture was stirred for 8 hours until room temperature. Water was then added to the mixture and the mixture was extracted with ethyl acetate. The organic phase was sequentially washed with water, a saturated aqueous solution of sodium bicarbonate, and a saturated aqueous solution of sodium chloride, and was dried with anhydrous sodium sulfate. The solvent was removed by distillation under reduced pressure and the residue was purified by silica gel column chromatography (hexane:ethyl acetate=2:1). In this manner, the desired product (2.00 g) was obtained as a colorless powder.

Reference Examples 27 and 28

Using the compounds of Reference Examples 24 and 25, the compounds shown below were each synthesized in the same manner as in Reference Example 26.

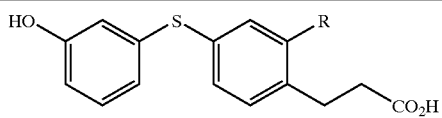

| Reference Example | R |
|---|---|
| 27 | Cl |
| 28 | CF$_3$ |

Reference Example 29

Benzyl 4'-(3-benzyloxyphenylthio)dihydrocinnamate

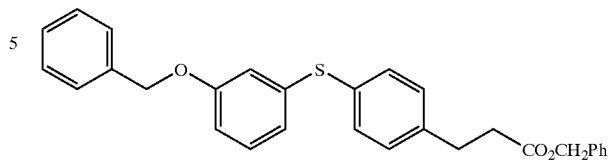

The compound of Reference Example 26 (2.00 g) was dissolved in DMF (30 mL), and benzyl bromide (2.4 mL) and potassium carbonate (2.00 g) were added to the solution. The mixture was stirred at 60° C. for 2 hours. Water was then added to the mixture and the mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=5:1). In this manner, the desired product (2.29 g) was obtained as a colorless oil.

Reference Example 30

Benzyl 4'-(3-benzyloxyphenylthio)-2'-chlorodihydrocinnamate

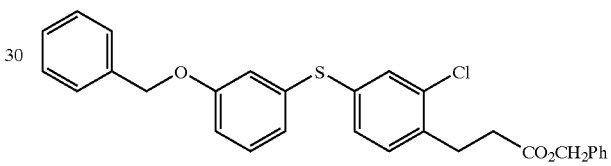

Using the compound of Reference Example 27, the reaction was carried out in the same manner as in Reference Example 29 to obtain the desired product as a yellow oil.

Reference Example 31

Methyl 4'-[(3-t-butyldimethylsiloxy)phenylthio]-2'-chlorodihydrocinnamate

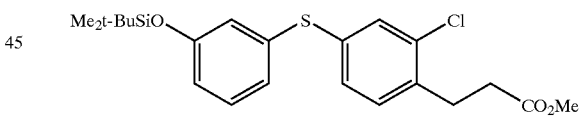

To a methanol solution (70 mL) of the compound of Reference Example 27 (6.20 g), thionyl chloride (2.2 mL) was added dropwise and the mixture was refluxed for 1 hour. The solvent was removed by distillation under reduced pressure to obtain a methyl ester as a colorless oil (5.80 g). The resulting, ester (5.80 g) was dissolved in DMF (80 mL) to form a solution. To this solution, imidazole (1.57 g) and t-butyldimethylchlorosilane (3.47 g) were added at 0° C. and the mixture was stirred for 7 hours until room temperature was reached. Subsequently, water was added to the mixture and the mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=5:1). In this manner, the desired product (7.26 g) was obtained as a colorless oil.

Reference Example 32
Ethyl 4'-(3-benzyloxyphenylthio)-2'-trifluoromethyldihydrocinnamate

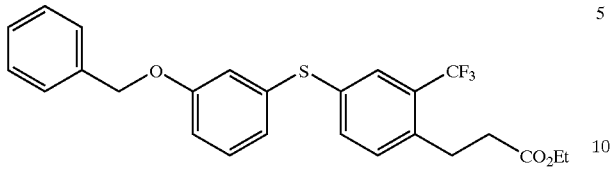

Using ethanol, the compound of Reference Example 28 was subjected to the same process as that of Reference Example 31 to synthesize an ethyl ester, which in turn was subjected to the same process as that of Reference Example 29 to obtain a pale yellow oil.

Reference Example 33
Ethyl 4'-(3-chlorophenylthio)dihydrocinnamate

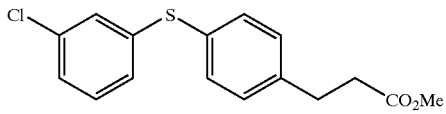

Under argon, the compound of Reference Example 18 (3.60 g) was dissolved in methanol (50 mL). Magnesium (500 mg) was then added to the solution while the solution was stirred at 10° C. The solution was stirred for another 1 hour at this temperature, followed by addition of magnesium (250 mg) and further stirring for 3 hours. Subsequently, diluted hydrochloric acid was added to the reaction mixture and the mixture was extracted with ethyl acetate. The organic phase was sequentially washed with water and a saturated aqueous solution of sodium chloride and was dried with anhydrous sodium sulfate. The solvent was removed by distillation under reduced pressure to obtain the desired product (3.13 g) as a pale yellow oil.

Reference Example 34
Methyl 4'-(3-trifluoromethyl-5-methylphenylthio)dihydrocinnamate

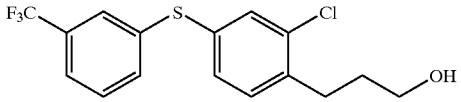

Using the compound of Reference Example 13, the reaction was carried out in the same manner as in Reference Example 33 to obtain the desired product as a colorless oil.

Reference Example 35
2'-chloro-4'-(3-trifluoromethylphenylthio)dihydrocinnamyl Alcohol

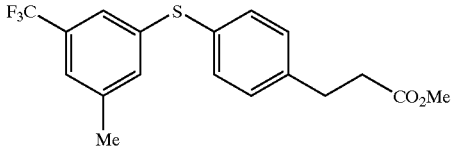

The compound of Reference Example 19 (1.50 g) was dissolved in THF (30 mL). Lithium aluminum hydride (200 mg) was then added to the solution while the solution was stirred at 0° C. After 30 minutes, a 20% NaOH solution was added and the crystallized inorganic deposits were removed by filtration through celite. The filtrate was extracted with ethyl acetate and the organic phase was sequentially washed with water and a saturated aqueous solution of sodium chloride and was dried with anhydrous sodium sulfate. The solvent was removed by distillation under reduced pressure to obtain the desired product (1.38 g) as a colorless oil.

Reference Examples 36 through 45

Using the compounds of Reference Examples 20 through 22, 24, and 29 through 34, the reactions were carried out in the same manner as in Reference Example 35 to synthesize the compounds shown in Table 4 below.

TABLE 4

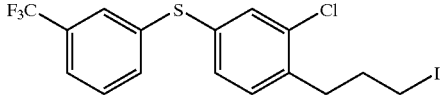

| Reference Example | R1 | R2 | R3 |
|---|---|---|---|
| 36 | $CF_3$ | H | H |
| 37 | $CF_3$ | H | $CF_3$ |
| 38 | $CF_3$ | $CF_3$ | Cl |
| 39 | $CF_3$ | Me | H |
| 40 | MeO | H | Cl |
| 41 | $PhCH_2O$ | H | H |
| 42 | $PhCH_2O$ | H | Cl |
| 43 | $PhCH_2O$ | H | $CF_3$ |
| 44 | $t\text{-BuMe}_2SiO$ | H | Cl |
| 45 | Cl | H | H |

Reference Example 46
2'-chloro-4'-(3-trifluoromethylphenylthio)dihydrocinnamyl Iodide The compound of Reference Example 35 (1.38 g) was dissolved in THF (20 mL). Imidazole (545 mg), triphenylphosphine (2.10 g) and iodine (2.00 g) were added to the solution while the solution was stirred at 0° C. The reaction mixture was further stirred for 2 hours at this temperature and another 1.5 hours at room temperature, followed by the addition of imidazole (160 mg), triphenylphosphine (600 mg) and iodine (500 mg). The mixture was subsequently stirred overnight. Water and then sodium thiosulfate were added to the reaction mixture, followed by extraction with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=50:1). In this manner, the desired product (1.55 g) was obtained as a colorless oil.

Reference Examples 47 through 56

Using the compounds of Reference Examples 36 through 45, the reactions were carried out in the same manner as in Reference Example 46 to synthesize the compounds shown in Table 5 below.

TABLE 5

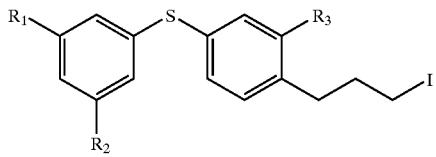

| Reference Example | R1 | R2 | R3 |
|---|---|---|---|
| 47 | $CF_3$ | H | H |
| 48 | $CF_3$ | H | $CF_3$ |
| 49 | $CF_3$ | $CF_3$ | Cl |
| 50 | $CF_3$ | Me | H |
| 51 | MeO | H | Cl |
| 52 | $PhCH_2O$ | H | H |
| 53 | $PhCH_2O$ | H | Cl |
| 54 | $PhCH_2O$ | H | $CF_3$ |
| 55 | $t\text{-}BuMe_2SiO$ | H | Cl |
| 56 | Cl | H | H |

Reference Example 57

4'-(3-benzyloxyphenylthio)-2'-chlorophenethyl Iodide

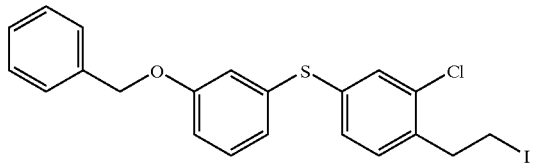

Reference Example 57-1

2'-chloro-4'-(3-methoxyphenylthio)benzyl Cyanide

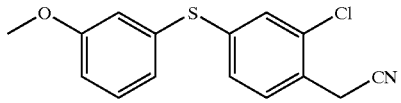

The compound of Reference Example 7 was treated in the same manner as in Reference Example 35 to obtain an alcohol. The alcohol (5.64 g) was dissolved in methylene chloride (100 mL) and phosphorus tribromide (2.25 mL) was added dropwise. The mixture was stirred at room temperature for 1 hour, followed by addition of ice water and extraction with ethyl acetate. The organic phase was sequentially washed with water and a saturated aqueous solution of sodium chloride and was dried with anhydrous sodium sulfate. The solvent was removed by distillation to obtain a pale yellow oil. The oil and potassium cyanide (1.56 g) were dissolved in a mixed solvent of DMSO (25 mL) and water (10 mL) and the solution was stirred at 90° C. for 5 hours. Water was then added to the mixture and the mixture was extracted with ethyl acetate. The organic phase was sequentially washed with water and a saturated aqueous solution of sodium chloride and was dried with anhydrous sodium sulfate. The solvent was removed by distillation and the residue was purified by silica gel column chromatography (hexane:ethyl acetate=10:1). In this manner, the desired cyanide form (3.81 g) was obtained as a pale yellow oil.

Reference Example 57-2

Ethyl 2'-chloro-4'-(3-methoxyphenylthio)phenylacetate

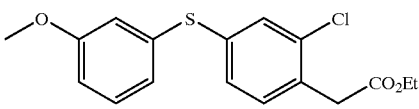

The above cyanide (3.81 g) and potassium hydroxide (3.68 g) were dissolved in a mixed solvent of ethanol (80 mL) and water (10 mL) and the solution was refluxed for 6 hours. The solution was then allowed to cool and the insoluble deposits were removed by filtration. The filtrate was neutralized with diluted hydrochloric acid and was extracted with ethyl acetate. The organic phase was sequentially washed with water and a saturated aqueous solution of sodium chloride and was dried with anhydrous sodium sulfate. The solvent was removed by distillation and ethanol (50 mL) and thionyl chloride (2 mL) were added to the resulting residue. The mixture was stirred at room temperature for 1 hour and the solvent was removed by distillation. The resulting residue was purified by silica gel column chromatography (hexane:ethyl acetate=10:1). In this manner, the desired ethyl ester form (3.89 g) was obtained as a colorless oil.

Reference Example 57-3

Ethyl 4'-(3-benzyloxyphenylthio)-2'-chlorophenyl Acetate

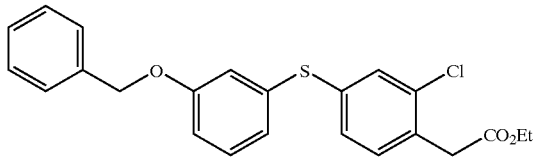

The desired ethyl ester was treated in the same manner as in Reference Example 26 and then in the same manner as in Reference Example 57-2 to form an ethyl ester, which in turn was subjected to the same process as that of Reference Example 29 to obtain a benzyl ether.

4'-(3-benzyloxyphenylthio)-2'-chlorophenethyl Iodide

The compound of Reference Example 57-3 was used as the starting material and was subjected to the same process as that of Reference Example 35 to obtain 4'-(3-benzyloxyphenylthio)-2'-chlorophenethyl alcohol, which in turn was subjected to the same process as that of Reference Example 46 to obtain the desired product as a colorless oil.

Reference Example 58

1-(3-benzyloxyphenylthio)-3-chloro-4-iodobutyl Benzene

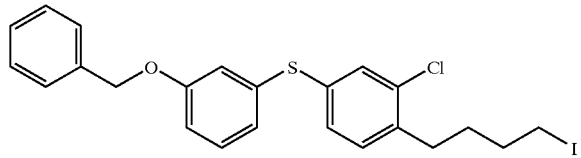

Reference Example 58-1
4-(3-benzyloxyphenylthio)-2-chlorophenethylaldehyde

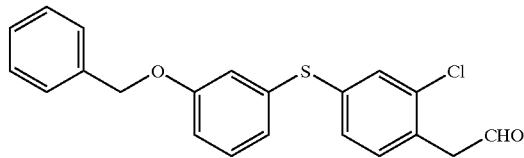

The compound of Reference Example 57-3 was subjected to alkaline hydrolysis and then to condensation with N,O-dimethylhydroxyamine to form an amid, which in turn was reduced in the same manner as in Reference Example 35 to obtain the aldehyde as a yellow oil.

Reference Example 58-2
Ethyl 4-[(3-benzyloxyphenylthio)-2-chlorophenyl]butyric Acid

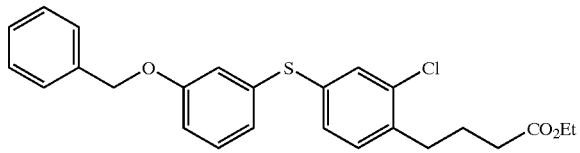

The compound of Reference Example 58-1 was treated in the same manner as in Reference Example 10 and then in the same manner as in Reference Example 19 to obtain the desired ethyl butyrate derivative.
1-(3-benzyloxyphenylthio)-3-chloro-4-iodobutylbenzene The compound of Reference Example 58-2 was used as the starting material and was subjected to the same process as that of Reference Example 57 to obtain the desired product as a colorless oil.

Reference Example 59
4'-(3-benzyloxyphenylthio)-2'-chlorobenzyl Bromide

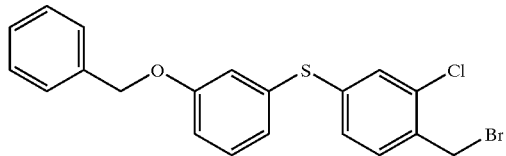

Reference Example 59-1
Ethyl 2-chloro-4-(3-hydroxyphenylthio)benzoate

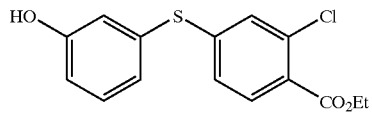

2-chloro-4-fluorobenzonitrile, in place of 2-chloro-4-fluorobenzaldehyde, was used in the same process as that of Reference Example 1 to obtain 2-chloro-4-(3-methoxyphenylthio)benzonitrile, which in turn was hydrolyzed in the same manner as in Reference Example 57-2. Then, in the same fashion as in Reference Example 26, methoxy group was removed from the reaction product and the product was subjected to esterification to obtain the desired product as a yellow oil.

Reference Example 59-2
4'-(3-benzyloxyphenylthio)-2'-chlorobenzyl Bromide

The compound of Reference Example 59-1 was subjected to the same process as that of Reference Example 29 to obtain a benzyl ether, which in turn was treated in the same manner as in Reference Example 35 to form an alcohol. Subsequently, using carbon tetrabromide in place of iodine, the reaction product was treated in the same manner as in Reference Example 46. In this manner, the desired product was obtained as a colorless oil.

Example 1
Ethyl 2-t-butoxycarbonylamino-5-[2-chloro-4-(3-trifluoromethylphenylthio)]phenyl-2-ethoxycarbonylpentanoate

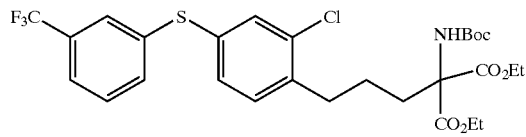

Under argon and at room temperature, sodium-t-butoxide (490 mg) was added to diethyl 2-t-butoxycarbonylaminomalonate (1.3 mL) dissolved in a mixed solvent of THF (35 mL) and DMF (4 mL). The mixture was then stirred at 80° C. for 20 minutes and was allowed to cool to room temperature. A solution of the compound of Reference Example 46 (1.55 g) in THF (5 mL) was added to the mixture. Subsequently, the mixture was refluxed for 5 hours and was then poured into ice water. The resulting mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=5:1). In this manner, the desired product (1.87 g) was obtained as a colorless oil.

$^1$H-NMR(400 MHz, CDCl$_3$) δ 1.22–1.36(6H, m), 1.42 (9H, s), 1.45–1.53(2H, m), 2.37(2H, br), 2.74(2H, t, J=7.8 Hz), 4.23(4H, m), 5.94(1H, s), 7.16–7.21(2H, m), 7.36–7.56 (5H, m)<

Examples 2 through 13

Using the compounds of Reference Examples 47 through 58, the reactions were carried out in the same manner as in Example 1 to synthesize the compounds shown in Table 6 below:

TABLE 6

| Example | R1 | R2 | R3 | n | Yield (%) | Characteristics |
|---|---|---|---|---|---|---|
| 2 | CF$_3$ | H | H | 3 | 90 | Colorless oil |
| 3 | CF$_3$ | H | CF$_3$ | 3 | 53 | Pale yellow oil |
| 4 | CF$_3$ | CF$_3$ | Cl | 3 | 66 | Colorless oil |
| 5 | CF$_3$ | Me | H | 3 | 100 | Colorless oil |
| 6 | MeO | H | Cl | 3 | 87 | Colorless oil |
| 7 | PhCH$_2$O | H | H | 3 | — | Colorless oil |

TABLE 6-continued

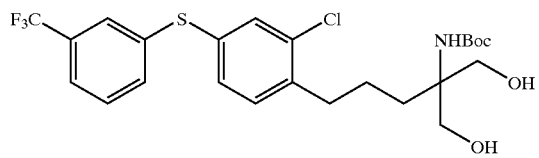

| Example | R1 | R2 | R3 | n | Yield (%) | Characteristics |
|---------|-----|----|-----|---|-----------|-----------------|
| 8 | PhCH$_2$O | H | Cl | 2 | 100 | Pale yellow oil |
| 9 | PhCH$_2$O | H | Cl | 3 | 100 | Colorless oil |
| 10 | PhCH$_2$O | H | Cl | 4 | 100 | Colorless oil |
| 11 | PhCH$_2$O | H | CF$_3$ | 3 | 100 | Colorless oil |
| 12 | t-BuMe$_2$SiO | H | Cl | 3 | — | Colorless oil |
| 13 | Cl | H | H | 3 | 82 | Colorless oil |

The mark "—" means yield is shown in Table 7 as a total yield.

Example 14
Ethyl 2-t-butoxycarbonylamino-2-ethoxycarbonyl-5-[4-(3-trifluoromethylphenylsulfinyl)]phenylpentanoate

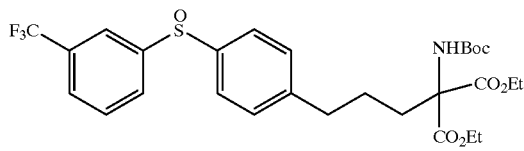

The compound of Example 2 (1.50 g) was dissolved in methylene chloride (80 mL) and, while the solution was stirred at 0° C., m-chloroperbenzoic acid (450 mg) was added in small portions. The resulting mixture was stirred for 1 hour at the same temperature and then another 2 hours at room temperature, followed by the addition of water. The resulting mixture was extracted with ethyl acetate. The organic phase was sequentially washed with a saturated aqueous solution of sodium bicarbonate and a saturated aqueous solution of sodium chloride and was dried with anhydrous sodium sulfate. The solvent was removed by distillation under reduced pressure and the residue was purified by silica gel column chromatography (hexane:ethyl acetate=1:1). In this manner, the desired product (1.10 g) was obtained as a colorless oil.

$^1$H-NMR(400 MHz, CDCl$_3$) δ 1.18–1.21(6H, m), 1.40 (9H, s), 1.44–1.52(2H, m), 2.30(2H, br), 2.66(2H, t, J=7.3 Hz), 4.14–4.22(4H, m), 5.91(1H, br), 7.27(2H, d, J=8.3 Hz), 7.56(2H, d, J=8.3 Hz), 7.59(1H, t, J=8.3 Hz), 7.69(1H, d, J=8.3 Hz), 7.78(1H, d, J=8.3 Hz), 7.95(1H, s)

Example 15
Ethyl 2-t-butoxycarbonylamino-5-[4-(3-trifluoromethyl-5-methylphenylsulfinyl)]phenyl-2-ethoxycarbonylpentanoate

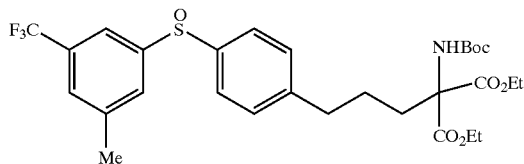

Using the compound of Example 5, the reaction was carried out in the same manner as in Example 14 to obtain the desired product as a colorless oil.

FABMS: 600 ([M+H]+) $^1$H-NMR(400 MHz, CDCl$_3$) δ 1.18–1.22(6H, m), 1.41(9H, s), 1.46–1.50(2H, m), 2.31(2H, br), 2.45(3H, s), 2.66(2H, t, J=7.3 Hz), 4.14–4.22(4H, m), 5.92(1H, br s), 7.27(2H, d, J=7.8 Hz), 7.48(1H, s), 7.55(2H, d, J=7.8 Hz), 7.62(1H, s), 7.70(1H, s)

Example 16
2-t-butoxycarbonylamino-2-[2-chloro-4-(3-trifluoromethylphenylthio)phenyl]propyl-1,3-propanediol The compound of Example 1 (1.87 g) was dissolved in THF (30 mL) and lithium borohydride (675 mg) was added to the solution while the solution was stirred at 0° C. Subsequently, ethanol (5 mL) was added to the solution and the mixture was stirred overnight while allowed to gradually warm to room temperature. Ice water was then added to the reaction mixture and the organic solvent was removed by distillation under reduced pressure. 10% aqueous citric acid was added to the residue to adjust the pH to 3 and the mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=1:1) to obtain the desired product (1.10 g) as a colorless oil.

FABMS: 520([M+H]+) $^1$H-NMR(400 MHz, CDCl$_3$) δ 1.43(9H, s), 1.62–1.65(4H, m), 2.72(2H, br), 3.31(2H, br), 3.57–3.62(2H, m), 3.81–3.85(2H, m), 4.93(1H, s), 7.20–7.27(3H, m), 7.38–7.55(4H, m)

Examples 17 through 30

Using the compounds of Examples 2 through 15, the reactions were carried out in the same manner as in Example 16 to synthesize the compounds shown in Table 7 below.

TABLE 7

| Example | R1 | R2 | R3 | X | n | Yield (%) | Characteristics |
|---------|-----|----|-----|---|---|-----------|-----------------|
| 17 | CF$_3$ | H | H | S | 3 | 89 | Colorless powder |
| 18 | CF$_3$ | H | H | SO | 3 | 71 | Colorless amorphous |
| 19 | CF$_3$ | H | CF$_3$ | S | 3 | 51 | Colorless oil |
| 20 | CF$_3$ | CF$_3$ | Cl | S | 3 | 66 | Colorless amorphous |
| 21 | CF$_3$ | Me | H | S | 3 | 81 | Colorless powder |
| 22 | CF$_3$ | Me | H | SO | 3 | 65 | Colorless powder |
| 23 | MeO | H | Cl | S | 3 | 56 | Colorless oil |
| 24 | PhCH$_2$O | H | H | S | 3 | (45) | Colorless oil |
| 25 | PhCH$_2$O | H | Cl | S | 2 | 41 | Colorless oil |
| 26 | PhCH$_2$O | H | Cl | S | 3 | 65 | Colorless oil |
| 27 | PhCH$_2$O | H | Cl | S | 4 | 76 | Colorless oil |
| 28 | PhCH$_2$O | H | CF$_3$ | S | 3 | 66 | Colorless oil |
| 29 | t-BuMe$_2$SiO | H | Cl | S | 3 | (33) | Colorless oil |
| 30 | Cl | H | H | S | 3 | 41 | Colorless oil |

In the parentheses, shown is the total yield of the two steps.

Example 31
5-t-butoxycarbonylamino-2,2-di-t-butyl-5-[(3-chlorophenylthio)phenyl]propyl-1,3,2-dioxasilane

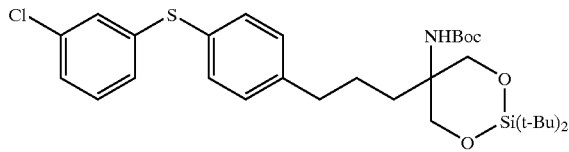

At 0° C., di-t-butylsilyl bis(trifluoromethanesulfonate) (0.55 mL) was added to a DMF solution (15 mL) containing the compound of Example 30 (490 mg) and 2,6-lutidine (0.35 mL). The mixture was stirred for 5 hours until room temperature and was poured into ice water. The mixture was then extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=8:1) to obtain the desired product (630 mg) as a colorless powder.

$^1$H-NMR(400 MHz, CDCl$_3$) δ 1.05(9H, s), 1.06(9H, s), 1.43(9H, s), 1.57–1.62(4H, m), 2.58(2H, br), 3.89(2H, d, J=10.7 Hz), 4.22(2H, d, J=10.7 Hz), 4.92(1H, br s), 7.09–7.20(6H, m), 7.34(2H, d, J=8.3 Hz)

Example 32
5-t-butoxycarbonylamino-2,2-di-t-butyl-5-[(3-chlorophenylsulfonyl)phenyl]propyl-1,3,2-dioxasilane

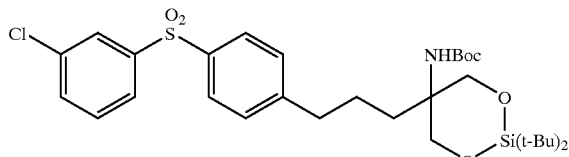

The compound of Example 31 was oxidized in the same manner as in Example 14 to obtain the desired product as a colorless powder.

$^1$H-NMR(400 MHz, CDCl$_3$) δ 1.04(9H, s), 1.05(9H, s), 1.41(9H, s), 1.55–1.57(4H, m), 2.63(2H, br), 3.86(2H, d, J=11.2 Hz), 4.19(2H, d, J=11.2 Hz), 4.92(1H, br), 7.29(2H, d, J=8.3 Hz), 7.44(1H, t, J=8.3 Hz), 7.50–7.53(1H, m), 7.80–7.85(1H, m), 7.84(2H, d, J=8.3 Hz), 7.91–7.92(1H, m)

Example 33
5-t-butoxycarbonylamino-5-[4-(3-t-butoxydimethylsiloxyphenylthio)-2-chlorophenyl]propyl-2,2-dimethyl-1,3-dioxane

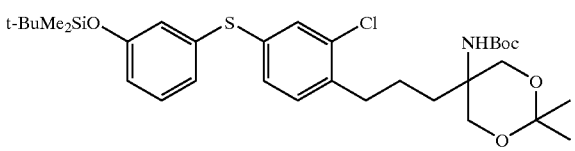

To a solution of the compound of Example 29 (1.88 g) in DMF (30 mL), 2,2-dimethoxypropane (2.5 mL) along with p-toluenesulfonic acid (100 mg) was added and the mixture was stirred for 5 hours while heated at 80° C. The reaction mixture was poured into water and was extracted with ethyl acetate. The organic phase was then sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=3:1) to obtain the desired product (1.11 g) as a colorless powder.

Example 34
5-t-butoxycarbonylamino-5-[2-chloro-4-(3-hydroxyphenylthio)phenyl]propyl-2,2-dimethyl-1,3-dioxane

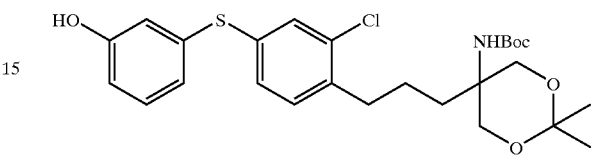

To a solution of the compound of Example 33 (1.10 g) in THF (20 mL), a 1 mol/L solution of tetrabutylammonium fluoride in THF (5 mL) was added. After 10 minutes, the reaction mixture was poured into water and was extracted with ethyl acetate. The organic phase was sequentially washed with water and a saturated aqueous solution of sodium chloride and was dried with anhydrous sodium sulfate. The solvent was removed by distillation under reduced pressure to obtain the desired product (900 mg) as a colorless powder.

$^1$H-NMR(400 MHz, CDCl$_3$) δ 1.39(9H, s), 1.40(3H, s), 1.41(3H, s), 1.60(4H, br s), 2.78(2H, br s), 3.64(2H, d, J=11.7 Hz), 3.83(2H, d, J=11.7 Hz), 4.89(1H, br), 7.27(1H, br), 6.53(1H, br), 6.65(1H, d, J=6.9 Hz), 6.85(1H, d, J=8.3 Hz), 7.11–7.16(2H, m), 7.26–7.28(1H, m), 7.45(1H, br s)

Example 35
5-t-butoxycarbonylamino-5-[2-chloro-4-(3-(3-chlorobenzyloxy)phenylthio)phenyl]propyl-2,2-dimethyl-1,3-dioxane

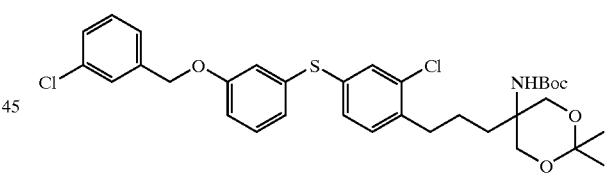

To a solution of the compound of Example 34 (500 mg) in DMF (10 mL), potassium carbonate (500 mg) and m-chlorobenzyl bromide (0.16 mL) were added and the mixture was stirred at 70° C. for 1 hour. The reaction mixture was then poured into water and was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=3:1) to obtain the desired product (520 mg) as a colorless powder.

$^1$H-NMR(400 MHz, CDCl$_3$) δ 1.41(3H, s), 1.42(12H, s), 1.53–1.56(2H, m), 1.76(2H, br), 2.69(2H, t, J=7.8 Hz), 3.65(2H, d, J=11.7 Hz), 3.88(2H, d, J=11.7 Hz), 4.88(1H, br), 4.99(2H, s), 6.86(1H, dd, J=8.3, 2.0 Hz), 6.92–6.95(2H, m), 7.11–7.16(2H, m), 7.21–7.32(5H, m), 7.40(1H, s)

Example 36

2-amino-2-[4-(3-benzyloxyphenylthio)-2-chlorophenyl]propyl-1,3-propanediol hydrochloride

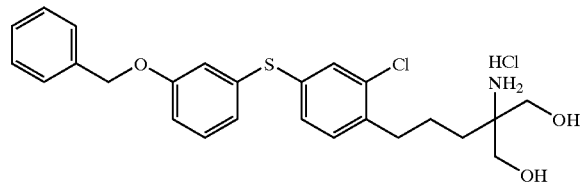

Ethyl acetate (100 mL) containing 3 mol/L hydrochloric acid was added to a methanol solution (150 mL) of the compound of Example 26 (6.91 g) and the mixture was stirred at room temperature for 1 hour. The solvent was removed by distillation under reduced pressure. A mixture of methylene chloride and hexane (methylene chloride:hexane=1:5) was added to the residue and the resultant crystals were collected by filtration. After drying, the desired product (5.75 g) was obtained as a colorless powder.

FABMS: 458 ([M+H]+) $^1$H-NMR(400 MHz, DMSO-$d_6$) δ 1.57(4H, br s), 2.64(2H, br s), 3.36–3.46(4H, m), 5.09(2H, s), 5.31(2H, t, J=4.9 Hz), 6.89(1H, d, J=8.3 Hz), 6.95(1H, t, J=2.0 Hz), 6.99(1H, dd, J=8.3 Hz, 2.0 Hz), 7.23(1H, dd, J=7.8 Hz, 2.0 Hz), 7.29(8H, m), 7.70(3H, br s) Melting point=132–133° C. (EtOH-iPr$_2$O) Elemental analysis (%): $C_{25}H_{28}ClNO_3S·HCl$

|  | C | H | N |
|---|---|---|---|
| Calcd. | 60.72 | 5.91 | 2.83 |
| Found | 60.71 | 5.85 | 2.91 |

Examples 37 through 45

Using the compounds of Examples 16 through 24, the reactions were carried out in the same manner as in Example 36 to synthesize the compounds shown in Table 8 below.

Example 46

2-amino-2-[4-(3-benzyloxyphenylthio)-2-chlorophenyl]ethyl-1,3-propanediol Hydrochloride

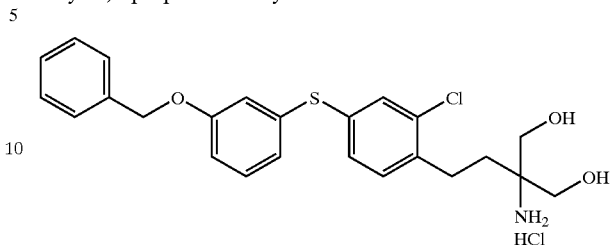

Using the compound of Example 25, the reaction was carried out in the same manner as in Example 36 to obtain the desired product.

$^1$H-NMR(400 MHz, DMSO-$d_6$) δ 1.75–1.79(2H, m), 2.69–2.73(2H, m), 3.54(2H, s), 5.10(2H, s), 5.40(2H, t, J=4.0 Hz), 6.91(1H, dd, J=8.3 Hz, 1.8 Hz), 6.96(1H, t, J=1.8 Hz), 7.00(1H, dd, J=8.3 Hz, 1.8 Hz), 7.26(1H, dd, J=8.8 Hz, 1.8 Hz), 7.30–7.42(8H, m), 7.82(3H, br) FABMS: 444([M+H]+) Melting point=143–145° C. (EtOH-iPr$_2$O) Elemental analysis (%): $C_{24}H_{26}ClNO_3S·HCl$

|  | C | H | N |
|---|---|---|---|
| Calcd. | 60.00 | 5.66 | 2.92 |
| Found | 59.88 | 5.61 | 2.97 |

Examples 47 through 51

Using the compounds of Examples 27, 28, 30, 32, and 35, the reactions were carried out in the same manner as in Example 36 to synthesize the compounds shown in Table 9 below.

TABLE 8

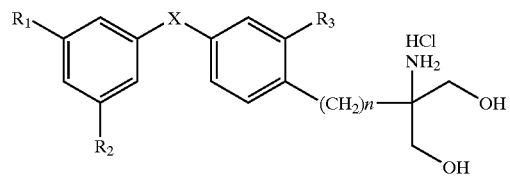

| Example | R1 | R2 | R3 | X | n | Yield (%) | Characteristics | FABMS [M + H]+ | Melting point ° C. |
|---|---|---|---|---|---|---|---|---|---|
| 37 | CF$_3$ | H | H | S | 3 | 94 | Colorless powder | 386 | 140–143 |
| 38 | CF$_3$ | H | H | SO | 3 | 97 | Colorless amorphous | 402 |  |
| 39 | CF$_3$ | H | Cl | S | 3 | 93 | Colorless powder | 420 | 194–197 |
| 40 | CF$_3$ | H | CF$_3$ | S | 3 | 83 | Colorless powder | 453 | 107–112 |
| 41 | CF$_3$ | CF$_3$ | Cl | S | 3 | 93 | Colorless powder | 488 | 159–162 |
| 42 | CF$_3$ | Me | H | S | 3 | 86 | Colorless powder | 400 | 117–119 |
| 43 | CF$_3$ | Me | H | SO | 3 | 88 | Colorless amorphous | 416 |  |
| 44 | MeO | H | Cl | S | 3 | 90 | Yellow powder | 382 | 98–100 |
| 45 | PhCH$_2$O | H | H | S | 3 | 100 | Colorless powder | 424 | 97–100 |

TABLE 9

| Example | R1 | R2 | R3 | X | n | Yield (%) | Characteristics | FABMS [M + H]+ | Melting point ° C. |
|---|---|---|---|---|---|---|---|---|---|
| 47 | PhCH$_2$O | H | Cl | S | 4 | 88 | Colorless powder | 472 | 91–93 |
| 48 | PhCH$_2$O | H | CF$_3$ | S | 3 | 85 | Colorless powder | 492 | 86–98 |
| 49 | 3-Cl-C$_6$H$_4$-CH$_2$O | H | Cl | S | 3 | 100 | Colorless powder | 492 | 95–98 |
| 50 | Cl | H | H | S | 3 | 77 | Colorless powder | 352 | 122–125 |
| 51* | Cl | H | H | SO$_2$ | 3 | 97 | Colorless powder | 384 | 171–174 |

*Carried out after Bu$_4$NF treatment.

Example 52
5-t-butoxycarbonylamino-5-[2-chloro-4-(3-benzyloxyphenylthio)phenyl]methyl-2,2-dimethyl-1,3-dioxane

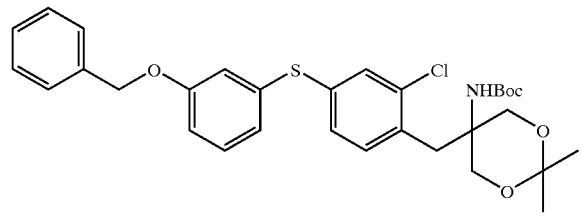

Using the compound of Reference Example 59, the reaction was carried out in the same manner as in Example 1 to synthesize an ester, which in turn was subjected to the same process as that of Reference Example 16 to be converted to a diol. Subsequently, the diol was treated in the same manner as in Example 35 to obtain the desired product as a yellow oil.

$^1$H-NMR(400 MHz, CDCl$_3$) δ 1.43(6H, s), 1.46(9H, s), 3.23(2H, s), 3.83(2H, d, J=11.7 Hz), 3.89(2H, d, J=11.7 Hz), 4.84(1H, br s), 5.03(2H, s), 6.91(1H, ddd, J=8.3 Hz, 2.4 Hz, 1.0 Hz), 6.95–6.99(2H, m), 7.12(1H, dd, J=8.3 Hz, 2.0 Hz), 7.22–7.41(8H, m)

Example 53
5-t-butoxycarbonylamino-5-[2-chloro-4-(3-benzyloxyphenylsulfinyl)phenyl]propyl-2,2-dimethyl-1,3-dioxane

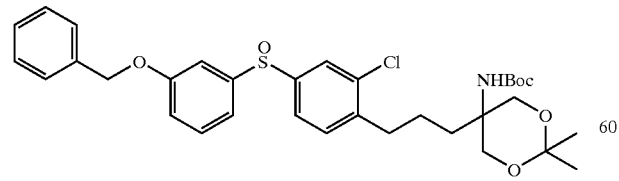

The compound of Example 26 was subjected to the reaction in the same manner as in Example 35 and was subsequently oxidized in the same fashion as in Example 14 to obtain the desired product as a colorless powder.

$^1$H-NMR(400 MHz, CDCl$_3$) δ 1.40(3H, s), 1.41(12H, s), 1.51–1.56(2H, m), 1.73–1.75(2H, m), 2.72(2H, t, J=7.8 Hz), 3.64(2H, d, J=11.7 Hz), 3.85(2H, d, J=11.7 Hz), 4.87(1H, br s), 5.09(2H, s), 7.05(1H, dd, J=8.3 Hz, 2.9 Hz), 7.19(1H, d, J=8.3 Hz), 7.22–7.42(9H, m), 7.59(1H, d, J=2.9 Hz)<

Example 54
5-t-butoxycarbonylamino-5-[2-chloro-4-(3-benzyloxyphenylsulfonyl)phenyl]propyl-2,2-dimethyl-1,3-dioxane

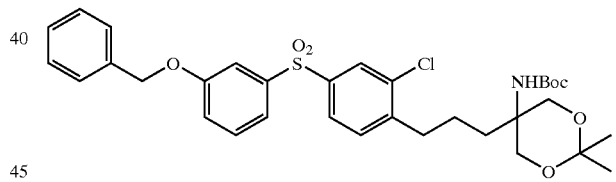

The compound of Example 53 was oxidized in the same manner as in Example 14 to obtain the desired product as a colorless powder.

$^1$H-NMR(400 MHz, CDCl$_3$) δ 1.40(3H, s), 1.41(12H, s), 1.53–1.60(2H, m), 1.73–1.75(2H, m), 2.74(2H, t, J=7.3 Hz), 3.64(2H, d, J=11.7 Hz), 3.84(2H, d, J=11.7 Hz), 4.87(1H, br s), 5.10(2H, s), 7.15(1H, dd, J=7.8 Hz, 1.5 Hz), 7.31–7.53(9H, m), 7.69(1H, dd, J=7.8 Hz, 2 Hz), 7.86(1H, d, J=1.5 Hz)

Examples 55 through 57

Using the compounds of Examples 52 through 54, the reactions were carried out in the same manner as in Example 36 to synthesize the compounds shown in Table 10 below.

TABLE 10

$$R_1\text{-}\underset{R_2}{\phantom{X}}\text{-}X\text{-}\underset{R_3}{\phantom{X}}\text{-}(CH_2)_n\text{-}C(NH_2\cdot HCl)(CH_2OH)_2$$

| Example | R1 | R2 | R3 | X | n | Yield (%) | Characteristics | FABMS [M + H]⁺ | Melting point ° C. |
|---|---|---|---|---|---|---|---|---|---|
| 55 | PhCH$_2$O | H | Cl | S | 1 | 88 | Colorless powder | 430 | 163–165 |
| 56 | PhCH$_2$O | H | Cl | SO | 3 | 85 | Pale brown amorphous | 474 | |
| 57 | PhCH$_2$O | H | Cl | SO$_2$ | 3 | 96 | Brown powder | 490 | 60–62 |

The following experiments were conducted to prove the effectiveness of the compounds of the present invention.

<Experiment 1>

Ability of Test Compounds to Suppress Graft Host vs Rejection in Mice

This experiment was performed according to the method described in *Transplantation*, 55, No. 3 (1993): 578–591. Spleens were collected from 9 to 11 week old male BALB/c mice (CLEA JAPAN Inc., CHARLES RIVER JAPAN Inc., or JAPAN SLC Inc.). The spleens were placed in a phosphate-buffered saline (PBS(−), NISSUI PHARMACEUTICAL Co., Ltd.) or in an RPMI-1640 medium (GIBCO INDUSTRIES Inc., or IWAKI GLASS Co., Ltd.) and were either passed through a stainless steel mesh, or gently pressed between two slide glasses and then passed through a cell strainer (70 μm, Falcon), to form a cell suspension. The suspension was then centrifuged and the supernatant was discarded. An ammonium chloride-Tris isotonic buffer was added to the suspension to lyse erythrocytes. The cells were then centrifuged and washed three times in PBS (−) or RPMI-1640 medium and were resuspended in an RPMI-1640 medium. To this suspension, mitomycin C (KYOWA HAKKO KOGYO Co., Ltd.) was added to a final concentration of 25 μg/mL and the suspension was incubated for 30 minutes at 37° C. in a 5% CO$_2$ atmosphere. The cells were again centrifuged and washed in PBS (−) or RPMI-1640 medium and were resuspended in an RPMI-1640 medium so that the medium would contain 2.5×10⁸ cells/mL. This suspension served as a "stimulation cell suspension." Using a 27G needle along with a microsyringe (Hamilton), 20 μL (5×10⁶ cells/mouse) of the stimulation cell suspension was subcutaneously injected into the right hind footpad of 7 to 9 week old male C3H/HeN mice (CLEA JAPAN Inc., CHARLES RIVER JAPAN Inc., or JAPAN SLC Inc.). A group of mice was injected with RPMI-1640 medium alone to serve as normal control. 4 days after the injection, right popliteal lymph nodes were collected and were weighed on a Mettler AT201 electronic scale (METTLER TOLEDO Co., Ltd.). Each animal was intraperitoneally administered a test compound once a day for four consecutive days starting on the day of the injection of the stimulation cells (i.e., total of 4 times). Controls were administered a vehicle that has the same composition as that used in the preparation of the test compounds. The results are shown in Table 11 below:

TABLE 11

| Example No. | Dose (mg/kg) | Inhibition (%) |
|---|---|---|
| 36 | 0.03 | 85 |
| 37 | 10 | 92 |
| 38 | 10 | 56 |
| 39 | 0.3 | 83 |
| 41 | 3 | 89 |
| 42 | 10 | 76 |
| 43 | 10 | 64 |
| 45 | 0.3 | 101 |
| 46 | 0.3 | 80 |
| 47 | 0.3 | 87 |
| 48 | 0.3 | 48 |
| 49 | 0.3 | 63 |
| 51 | 10 | 50 |

<Experiment 2>

Ability of Test Compounds to Suppress Delayed-Type Hypersensitivity in Mice.

This experiment was performed according to the method described in *Methods in Enzymology*, 300 (1999): 345–363. 1-fluoro-2,4-dinitrobenzene (DNFB, NACALAI TESQUE Inc.) was dissolved in a mixture of acetone and olive oil (acetone: olive oil=4:1) to a concentration of 1% (v/v). 10 μL of the 1% DNFB solution was applied to the footpad of each hind leg of male BALB/c mice (JAPAN SLC Inc. or CHARLES RIVER JAPAN Inc.) for sensitization. The sensitization was done for 2 consecutive days (day 0 and day 1). On day 5, the mice were challenged with the antigen to induce delayed-type hypersensitive responses: First, the initial thickness of each ear was measured by the dial thickness gauge G (0.01–10 mm, OZAKI MFG Co., Ltd.) and a test compound was administered. 30 minutes after the administration, 10 μL of a 0.2% (v/v) DNFB solution was applied to the inner and outer surfaces of the right ear of each animal for antigen challenge. The left ear of each animal was challenged with the solvent alone. 24 hours after the challenge, the increase in the ear thickness was measured for each ear and the difference in thickness between the right and the left ears was determined for each individual. The test compound was dissolved, or suspended, in an ultra pure water and was orally administered at a dose of 0.1 mL/10 g of body weight. A control group was administered ultra pure water alone. The results are shown in Table 12 below:

TABLE 12

| Example No. | Dose (mg/kg) | Inhibition (%) |
|---|---|---|
| 36 | 1 | 86 |
| 37 | 30 | 87 |
| 39 | 3 | 55 |
| 49 | 30 | 81 |

<Experiment 3>
Activities of Test Compounds on Skin Transplantation Model in Mice Effects of the test compounds were examined on skin transplantation model in mice. The experimental procedure was referred to the method described in *Journal of Experimental Biology*, 28, No. 3 (1951); 385–405.

First, dorsal skin from male DBA/2 mice were stripped of the fatty layer and the panniculus carnosus and, cut into circular grafts with a diameter of 8 mm. Next, graft bed, a circular area, approximately 8 mm in diameter, was prepared in the back of anesthetized male BALB/c mice with a scalpel while the skin was pinched by forceps. Each graft obtained from the DBA/2 mice was placed on the graft bed formed in the backs of the BALB/c mice and was secured with a strip of adhesive bandage while held down from the top. 6 days after transplantation, the bandage was removed and the graft was subsequently observed everyday. The activity of each compound was evaluated based on the length of the graft survival period, which is defined as the number of days for rejection. Each test compound was dissolved in ultra pure water and was orally administered once a day, starting from the day of transplantation. In a similar fashion, the control group was administered ultra pure water alone.

Figure 2:
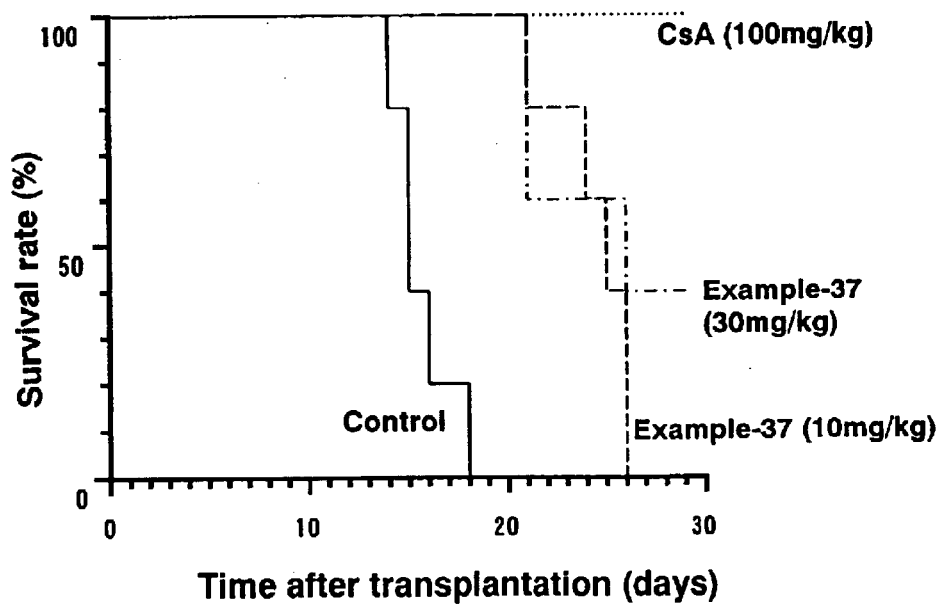
FIG. 2 is a graph showing activities of a test compound in a mouse skin graft model.
Figure 3:
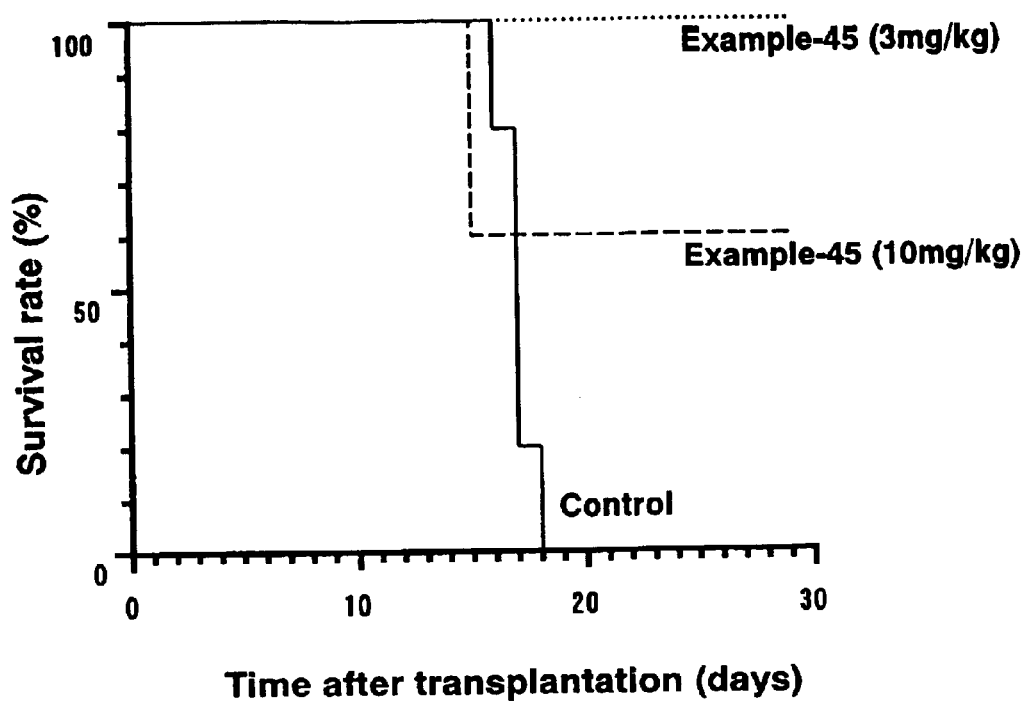
FIG. 3 is a graph showing activities of a test compound in a mouse skin graft model.

The results are shown in FIGS. 1 through 3.

As can be seen from the results, the compounds of the present invention represented by the general formula (1) have proven effective in animal model.

INDUSTRIAL APPLICABILITY

As set forth, the present invention has been devised in recognition of the fact that the novel diaryl sulfide derivatives, in particular those in which one of the aryl groups includes, at its para-position, a carbon chain with an aminopropanediol group and the other of the aryl groups includes a substituent at its meta-position, exhibit strong immunosuppressive effects. Effective immunosuppressors, the compounds of the present invention have a strong potential as a prophylactic or therapeutic agent against rejection in organ or bone marrow transplantation, autoimmune diseases, rheumatoid arthritis, psoriasis, atopic dermatitis, bronchial asthma, pollinosis and various other diseases.

What is claimed is:

1. A diaryl sulfide derivative, a pharmaceutically acceptable salt or hydrate thereof, the diaryl sulfide derivative represented by the following general formula (1):

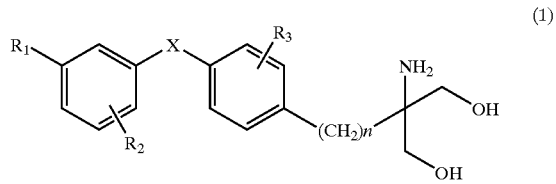

(1)

wherein $R_1$ is halogen, trihalomethyl, hydroxy, lower alkyl having 1 to 7 carbon atoms, phenyl, aralkyl, lower alkoxy having 1 to 4 carbon atoms, trifluoromethyloxy, substituted or unsubstituted phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; X is S, SO, or $SO_2$; and n is an integer from 1 to 4).

2. The diaryl sulfide derivative, pharmaceutically acceptable salt and hydrate thereof according to claim 1, wherein the compound of the general formula (1) is a compound represented by the following general formula (1a):

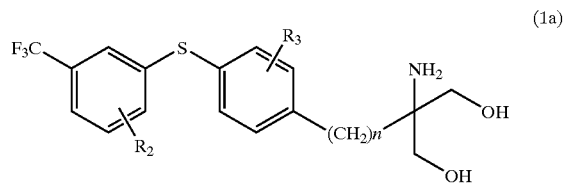

(1a)

wherein $R_2$, $R_3$, and n are the same as defined above.

3. The diaryl sulfide derivative, pharmaceutically acceptable salt and hydrate thereof according to claim 2, wherein $R_3$ is chlorine.

4. The diaryl sulfide derivative, pharmaceutically acceptable salt and hydrate thereof according to claim 2, wherein $R_3$ is trifluoromethyl.

5. The diaryl sulfide derivative, pharmaceutically acceptable salt and hydrate thereof according to claim 1, wherein the compound of the general formula (1) is a compound represented by the following general formula (1b):

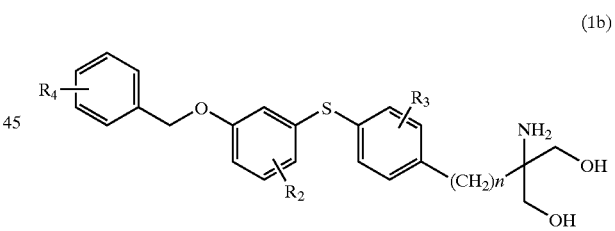

(1b)

wherein $R_2$, $R_3$, and n are the same as defined above; and $R_4$ is hydrogen, halogen, lower alkyl having 1 to 7 carbon atoms, lower alkoxy having 1 to 4 carbon atoms, or trifluoromethyl.

6. The diaryl sulfide derivative, pharmaceutically acceptable salt and hydrate thereof according to claim 5, wherein $R_3$ is chlorine.

7. The diaryl sulfide derivative, pharmaceutically acceptable salt and hydrate thereof according to claim 5, wherein $R_3$ is trifluoromethyl.

8. The diaryl sulfide derivative, pharmaceutically acceptable salt and hydrate thereof according to claim 1, wherein the compound of the general formula (1) is 1) 2-amino-2-[4-(3-benzyloxyphenylthio)-2-chlorophenyl]propyl-1,3-propanediol; 2) 2-amino-2-[4-(3-benzyloxyphenylthio) phenyl]propyl-1,3-propanediol; 3)2-amino-2-[4-(3-benzyloxyphenylthio)-2chlorophenyl]ethyl-1,3- propanediol; 4) 2-amino-2-[4-(3 benzyloxyphenylthio)-2-chlorophenyl]butyl-1,3-propanediol; 5)2-amino-2-[4-(3-(3'-chlorobenzyloxy)phenylthio)-2chlorophenyl]propyl-1,3-propanediol; 6) 2-amino-2-[4-(3benzyloxyphenylthio)-2-trifluoromethylphenyl]propyl-1,3propanediol; 7) 2-amino-2-[4-(3,5-bistrifluoromethyl-2chlorophenylthio)phenyl] propyl-1,3-propanediol; 8) 2-amino-2[4-(3-trifluoromethylphenylthio)phenyl]propyl-1,3-propanediol; 9) 2-amino-2-[2-chloro-4-(3trifluoromethylphenylthio) phenyl]propyl-1,3-propanediol; or 10) 2-amino-2-[2-trifluoromethyl-4-(3trifluoromethylphenylthio)phenyl] propyl-1,3-propanediol.

9. An immunosuppressive agent containing as an active ingredient at least one of a diaryl sulfide derivative, a pharmaceutically acceptable salt and a hydrate thereof, the diaryl sulfide derivative represented by the following general formula (1):

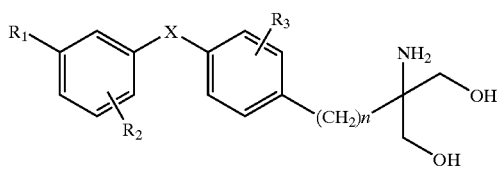

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy phenoxy, cyclohexylmethyloxy, substitutedor unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; and X is S, SO, or $SO_2$; and n is an integer from 1 to 4.

10. The immunosuppressive agent according to claim 9, containing as an active ingredient at least one of a diaryl sulfide derivative, a pharmaceutically acceptable salt and a hydrate thereof, wherein the compound of the general formula (1) is a compound represented by the following general formula (1a):

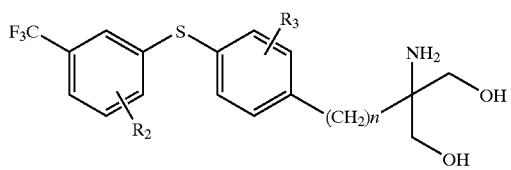

(1a)

wherein $R_2$, $R_3$, and n are the same as defined above.

11. The immunosuppressive agent according to claim 9, containing as an active ingredient at least one of a diaryl sulfide derivative, a pharmaceutically acceptable salt and a hydrate thereof, wherein the compound of the general formula (1) is a compound represented by the following general formula (1b):

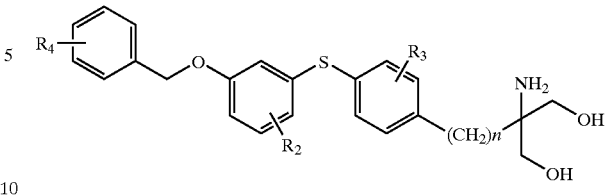

(1b)

wherein $R_2$, $R_3$, and n are the same as defined above; and $R_4$ is hydrogen, halogen, lower alkyl having 1 to 7 carbon atoms, lower alkoxy having 1 to 4 carbon atoms, or trifluoromethyl.

12. A method for the prophylactic or therapeutic treatment of autoimmune diseases which comprises administering to a patient in need of same, an immunosuppressive agent containing as an active ingredient at least one of a diaryl sulfide derivative, a pharmaceutically acceptable salt and a hydrate thereof, the diaryl sulfide derivative represented by the following general formula (1):

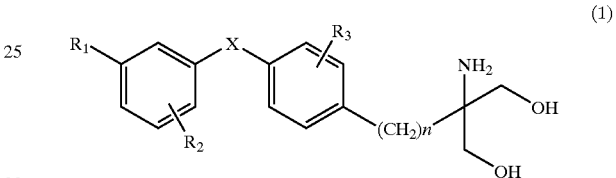

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy phenoxy, cyclohexylmethyloxy, substitutedor unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; and X is S, SO, or $SO_2$; and n is an integer from 1 to 4.

13. A method for the prophylactic or therapeutic treatment of rheumatoid arthritis which comprises administering to a patient in need of same, an immunosuppressive agent containing as an active ingredient at least one of a diaryl sulfide derivative, a pharmaceutically acceptable salt and a hydrate thereof, the diaryl sulfide derivative represented by the following general formula (1):

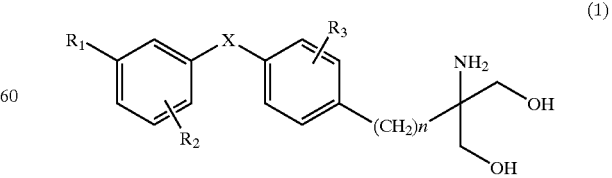

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy phenoxy, cyclohexylmethyloxy, substitutedor unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; and X is S, SO, or $SO_2$; and n is an integer from 1 to 4.

14. A method for prophylactic or therapeutic treatment of psoriasis or atopic dermatitis which comprises administering to a patient in need of same, an immunosuppressive agent containing as an active ingredient at least one of a diaryl sulfide derivative, a pharmaceutically acceptable salt and a hydrate thereof, the diaryl sulfide derivative represented by the following generated formula (1):

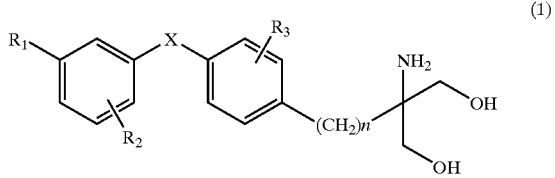

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy phenoxy, cyclohexylmethyloxy, substitutedor unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; and X is S, SO, or $SO_2$; and n is an integer from 1 to 4.

15. A method for prophylactic or therapeutic treatment of bronchial asthma or pollinosis which comprises administering to a patient in need of same, an immunosuppressive agent containing as an active ingredient at least one of a diaryl sulfide derivative, a pharmaceutically acceptable salt and a hydrate thereof, the diaryl sulfide derivative represented by the following general formula (1):

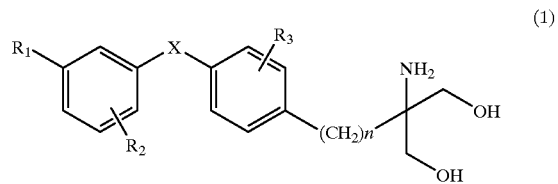

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy phenoxy, cyclohexylmethyloxy, substitutedor unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; and X is S, SO, or $SO_2$; and n is an integer from 1 to 4.

16. A method for prophylactic or therapeutic treatment against rejection in organ or bone marrow transplantation which comprises administering to a patient in need of same, an immunosuppressive agent containing as an active ingredient at least one of a diaryl sulfide derivative, a pharmaceutically acceptable salt and a hydrate thereof, the diaryl sulfide derivative represented by the following general formula (1):

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy phenoxy, cyclohexylmethyloxy, substitutedor unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, or lower alkoxymethyl having 1 to 4 carbon atoms; and X is S, SO, or $SO_2$; and n is an integer from 1 to 4.

* * * * *

UNITED STATES PATENT AND TRADEMARK OFFICE
CERTIFICATE OF CORRECTION

PATENT NO. : 6,960,692 B2  
APPLICATION NO. : 10/489820  
DATED : November 1, 2005  
INVENTOR(S) : Yasushi Kohno et al.

Page 1 of 1

It is certified that error appears in the above-identified patent and that said Letters Patent is hereby corrected as shown below:

In the specification, col. 28, please replace table 11 with the following:

--

TABLE 11

| Example No. | Dose (mg/kg) | Inhibition (%) |
|---|---|---|
| 36 | 0.03 | 85 |
| 37 | 10 | 92 |
| 38 | 10 | 56 |
| 39 | 3 | 83 |
| 41 | 3 | 89 |
| 42 | 10 | 76 |
| 43 | 10 | 64 |
| 45 | 0.3 | 101 |
| 46 | 0.3 | 80 |
| 47 | 0.3 | 87 |
| 48 | 0.3 | 48 |
| 49 | 0.3 | 63 |
| 51 | 10 | 50 |

--, wherein the fourth entry in the middle column has been changed from "0.3" to --3--.

Signed and Sealed this

First Day of December, 2009

David J. Kappos  
*Director of the United States Patent and Trademark Office*